United States Patent
Katsuyama

(10) Patent No.: US 8,260,867 B2
(45) Date of Patent: Sep. 4, 2012

(54) DATA MANAGEMENT SYSTEM FOR AN ANALYZING APPARATUS

(75) Inventor: Yuji Katsuyama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 198 days.

(21) Appl. No.: 12/282,258

(22) PCT Filed: Mar. 23, 2006

(86) PCT No.: PCT/JP2006/305791

§ 371 (c)(1),
(2), (4) Date: Sep. 9, 2008

(87) PCT Pub. No.: WO2007/108120

PCT Pub. Date: Sep. 27, 2007

(65) Prior Publication Data

US 2009/0037549 A1    Feb. 5, 2009

(51) Int. Cl.
G06F 15/16    (2006.01)
(52) U.S. Cl. .................................................. 709/206
(58) Field of Classification Search .................. 709/206, 709/207

See application file for complete search history.

(56) References Cited

U.S. PATENT DOCUMENTS

| | | | |
|---|---|---|---|
| 6,404,880 B1 * | 6/2002 | Stevens | 379/221.11 |
| 2002/0082480 A1 | 6/2002 | Riff et al. | |
| 2002/0120310 A1 | 8/2002 | Linden et al. | |
| 2002/0165952 A1 * | 11/2002 | Sewell et al. | 709/224 |
| 2002/0184041 A1 * | 12/2002 | Muller | 705/1 |
| 2004/0138920 A1 | 7/2004 | Sawanaga et al. | |
| 2005/0183143 A1 * | 8/2005 | Anderholm et al. | 726/22 |
| 2006/0089929 A1 * | 4/2006 | Morikawa | 707/4 |
| 2006/0165289 A1 * | 7/2006 | Boss et al. | 382/182 |
| 2011/0054864 A1 * | 3/2011 | Lundstedt et al. | 703/2 |

FOREIGN PATENT DOCUMENTS

CA    2 419 501 A1    3/2002

(Continued)

OTHER PUBLICATIONS

Written Opinion of the International Searching Authority dated Jul. 4, 2006, issued in corresponding International application No. PCT/JP2006/305791.

*Primary Examiner* — Jason Recek

(74) *Attorney, Agent, or Firm* — Sughrue Mion, PLLC

(57) ABSTRACT

When an analysis is finished in the GC/MS 11, which is an analyzing apparatus, and a file including the data obtained by the analysis is created by the analysis data file creator 13, the file transfer processor 14 sends the file to the web server 2 by way of the intranet 4. The file transfer processor 22 converts the data received into a format capable of being posted on a web page and stores it in the memory 21, and simultaneously notifies the analysis unit 1 of a link address for reading it out. The e-mail creation processor 15 creates an e-mail with the link address in the body and sends it to a predetermined mail address. The user receives and opens the e-mail on the mailer 31 of the client terminal 3 and clicks a link address corresponding to the desired analysis data. In response to this operation, the web server 2 sends the corresponding data to the terminal 3, which allows the analysis data to be viewed by the web browser 32.

2 Claims, 3 Drawing Sheets

FOREIGN PATENT DOCUMENTS

| | | |
|---|---|---|
| JP | 2006-048404 A | 2/2002 |
| JP | 2002-073399 A | 3/2002 |
| JP | 2002-133046 A | 5/2002 |
| JP | 2004-526466 A | 9/2004 |
| JP | 2005-110794 A | 4/2005 |
| JP | 2005-283526 A | 10/2005 |
| WO | 02/17777 A2 | 3/2002 |

* cited by examiner

US 8,260,867 B2

DATA MANAGEMENT SYSTEM FOR AN ANALYZING APPARATUS

TECHNICAL FIELD

The present invention relates to a data management system for managing data obtained by various kinds of analyzing apparatus, such as a chromatograph, mass spectrometer, and spectrophotometer, so that users can use the data. In particular, the present invention is chiefly preferable for a system which handles the data obtained by an automatic analyzing apparatus for continuously performing an analysis over a long period of time or for performing analyses by changing a number of samples.

BACKGROUND ART

Recently, a general personal computer has been used for controlling various analyzing apparatus such as a gas chromatograph, liquid chromatograph, and mass spectrometer and for data processing. Given this factor, in many cases, each piece of the analysis data obtained by such an analyzing apparatus and the analytical data obtained by performing various analytical processes based on the analysis data is electronically stored as a data file in a storage unit such as a hard disk. In addition, networking a personal computer connected to such an analyzing apparatus and other personal computers has been rapidly promoted. A popular configuration is the following: analysis data obtained by an analyzing apparatus and stored in a personal computer directly connected thereto are read out from another personal computer through a network to confirm the contents or use the data for reference in the subsequent analysis (for example, refer to Patent Document 1 or other documents).

In the case where the pieces of analysis data and analytical data as described earlier are stored in a standard file format, e.g. in a Word or Excel file format provided by Microsoft Corporation, it is very convenient in that the data contents can be viewed not only by a specified personal computer but also by a common personal computer, since applications software for opening the data in such a file format are included in most general personal computers. However, it is necessary to specify a file name to read out an intended data file, and the file name must be accurately entered. Hence, among the persons who use this feature, the file naming convention and other rules are required to be standardized. In addition, even if the file name is known, in the case where the file's existence location (i.e. in which folder of which personal computer) is unknown, an operation such as a search with the file name is required. If the amount of stored data is enormous, such a search takes a considerable amount of time, which leads to low work efficiency.

In the meantime, the use of dedicated application software for managing data files such as analysis data enables the search of the intended file in a shorter amount of time. In the case where this method is used, the same application software may be installed in all personal computers to be used. In practice, however, since such software is often updated on an irregular base, different versions of software can be easily mixed. In such a case, there is the possibility that, data files created and registered on old versions of the software may be read out using newer versions of the software, however conversely, data files created and registered on new versions of the software may not be read out on older versions of the software. In order to avoid such a situation, managing the application software's version or other method is required, which is troublesome in management and maintenance.

[Patent Document 1] Japanese Unexamined Patent Application Publication No. 2005-283526

DISCLOSURE OF THE INVENTION

Problem to be Solved by the Invention

The present invention has been developed to solve the aforementioned problem and the purpose thereof is to provide a data management system for an analyzing apparatus, which allows a user, on a personal computer without special application software, to promptly access desired analysis data and view them without requiring a troublesome and time-consuming operation such as a search.

Means for Solving the Problem

The present invention to solve the aforementioned problem provides a data management system for an analyzing apparatus, including: a computer for controlling/processing, which is intended for controlling an analyzing apparatus and receiving data obtained by the apparatus; a web server realized by the computer itself or by another computer connected to the computer so that they can mutually communicate; and a network in which they are connected, wherein:
the computer for controlling/processing includes:
a data transfer means for transferring a data file created in accordance with a performance of an analysis by the analyzing apparatus to the web server; and
an e-mail creator for creating an e-mail including link information sent from the web server in correspondence to a data transfer by the data transfer means and for sending the e-mail over the network to a predetermined e-mail address; and,
the web server includes:
a web data storing means for converting the data file sent from the data transfer means into a data format viewable on a web and for storing it;
a link information notifier for returning link information for reading out data stored in the web data storing means to the computer for controlling/processing; and
an access processor for, in the case where a readout command presenting link information regarding data stored in the web data storing means is received through the network, reading out data corresponding thereto and for sending them to a command source.

The network may be either an intranet system or the Internet. In the case where the computer for controlling/processing and a computer on which the web server is constructed are different, their mutual communication may be performed through the network or may be realized through another communication path.

Effects of the Invention

In the data management system for an analyzing apparatus according to the present invention, another client terminal is connected to the network, and the data stored in the web server are viewed through this client terminal. The client terminal is a personal computer with a general web browser and mailer. The user who views the analysis data in advance registers his or her e-mail address to the e-mail creator in the computer for controlling/processing.

When the analyzing apparatus performs an analysis and analysis data are obtained under the control of the computer for controlling/processing, the data transfer means transfers the data file including the analysis data to the web server. The data file may include processed data in which some sort of processing has been performed and analytical data in which an analytical process has been performed, other than raw data obtained by the analysis. The web data storing means in the web server converts the data file received into a format viewable on the web, e.g. into an HTML format, and stores it. Then the link information notifier notifies the computer for controlling/processing of the link information, which is determined in accordance with the storing.

The e-mail creator in the computer for controlling/processing creates an e-mail including the link information notified, and sends the e-mail to a predetermined e-mail address. Therefore, the e-mail is sent to the user whose e-mail address has been registered in advance. The e-mail is ultimately delivered to the client terminal in the user's hand through the network, and when the user opens the e-mail on the mailer, he or she finds the link information in it. When the link information is clicked by a mouse or other means for example, this command is sent to the web server through the network, and the access processor reads out the corresponding data and sends them to the command source, i.e. the client terminal. Hence, the user can freely view the analysis data stored in the web server by using the web browser included in the client terminal.

As just described, with the data management system for an analyzing apparatus according to the present invention, the user can view desired analysis data quite easily, i.e. without caring at all about a file name or other information as before, by using a personal computer with a general web browser and mailer. In addition, if an e-mail is to be sent to plural destinations, the desired analysis data can also be simultaneously viewed on plural terminals (i.e. personal computers). What is more, since no special application software is required to be installed in each client terminal and such special software is installed only on the web server and computer for controlling/processing, the system management is simple.

In one embodiment of the data management system for an analyzing apparatus according to the present invention, the e-mail creator may create and send one e-mail for every receipt of link information corresponding to the transfer of a data file after the completion of one analysis.

With this configuration, an e-mail is sent to the client terminal quickly after an analysis is completed, which allows the user to view the analysis data without much delay.

On the other hand, in a chromatographic analysis or other analyses, in many cases, a number of prepared samples are automatically changed and taken, while the analysis for each sample is sequentially performed. If the number of samples is vast in such a continuous analysis, the number of e-mails that the user (i.e. the receiver of the e-mails) receives will also be vast, which makes the operation even more complicated.

Given this factor, in another embodiment of the data management system for an analyzing apparatus according to the present invention, in the case where a plurality of analyses are sequentially performed by the analyzing apparatus, the e-mail creator puts together, when all of a series of the analyses are completed, pieces of link information received in correspondence to transfers of data files for all the analyses and sends them in one e-mail.

With this configuration, plural pieces of the link information corresponding to the data files of a series of a continuous analysis are collectively sent to the client terminal. This reduces the number of e-mails to be received, which eliminates the complexity of the user's operation even if the number of samples is vast.

The data management system for an analyzing apparatus according to the present invention can be used for a variety of analyzing apparatuses. However, its necessity is low in the case where the analysis time is short enough that the person in charge of the analysis (i.e. the user) has no time to leave the analyzing apparatus. Conversely, it is particularly useful for an analyzing apparatus that requires time for an analysis such as a liquid chromatograph and gas chromatograph for example, and that performs an analysis while automatically selecting and changing a number of samples as described earlier and requires a long analysis time as a whole. In the case where such an analyzing apparatus is used, users often leave the analyzing apparatus' side to perform another operation or to take a break. The use of the present invention allows the user to check the analysis data at any location away from the analyzing apparatus.

BEST MODE FOR CARRYING OUT THE INVENTION

Hereinafter, an embodiment of the management system for an analyzing apparatus according to the present invention will be described with reference to the figures. In this example, a gas chromatograph mass spectrometer (GC/MS) is used as the analyzing apparatus.

Figure 1:
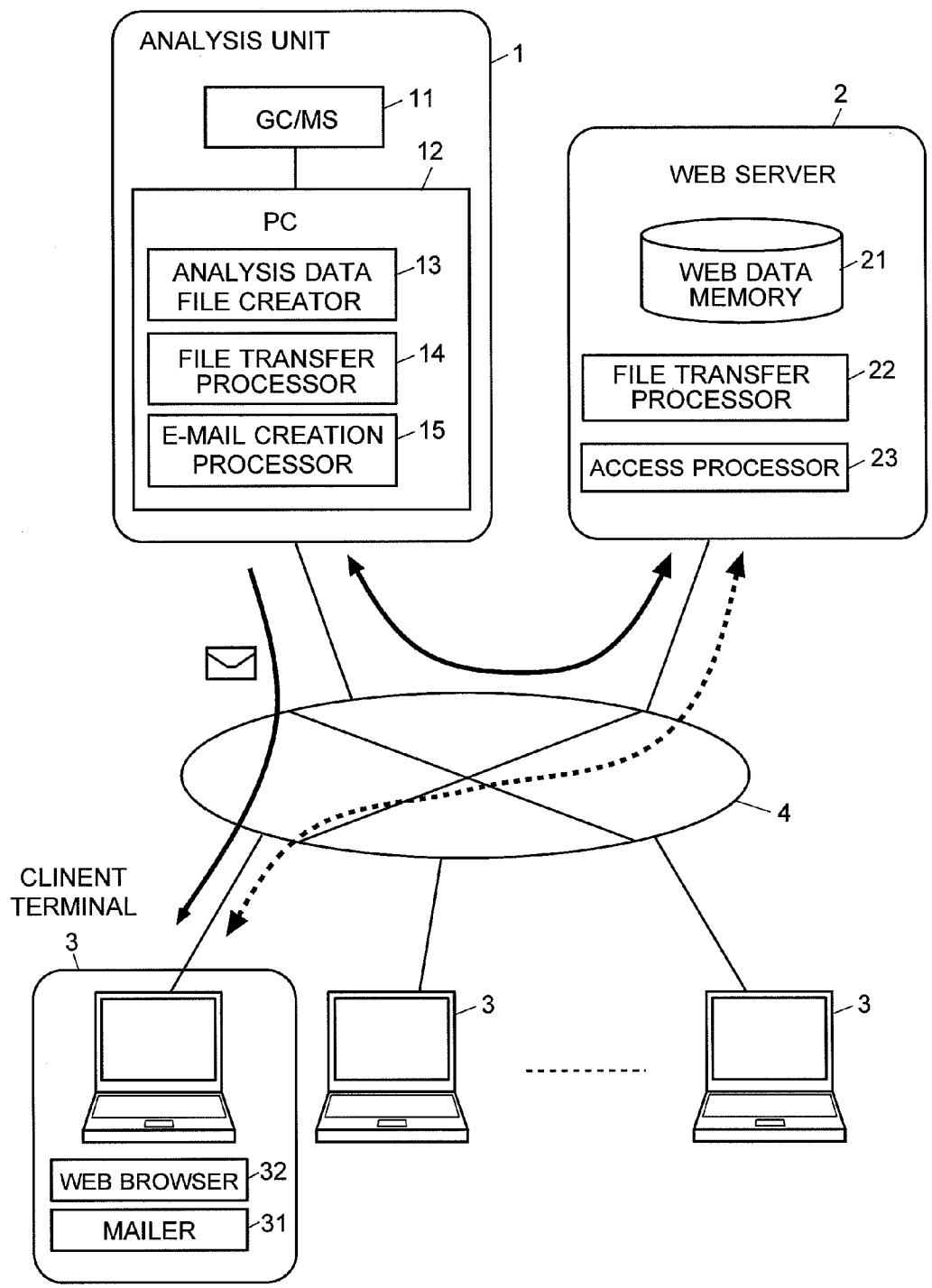
FIG. 1 is an overall configuration diagram of the data management system for an analyzing apparatus as an embodiment of the present invention.

FIG. 1 is an overall configuration diagram of the data management system according to the present embodiment. In the data management system, the analysis unit 1 includes a GC/MS 11 for performing an analysis for a sample to obtain data, and a personal computer (PC) 12 for controlling the operation of the GC/MS 11 and for performing a predetermined data processing function in response to the data obtained. The PC 12 has predetermined dedicated application software, and includes, as its functions, an analysis data file creator 13, a file transfer processor 14, and an e-mail creation processor 15.

The web server 2 is a computer with dedicated application software, and includes a web data memory 21, a file transfer processor 22, and an access processor 23. The PC 12 and the web server 2 in the analysis unit 1 are connected to an intranet 4, and other than these, client terminals 3 which include many personal computers are also connected to the intranet 4. Although not illustrated, a mail server and other units are presumed to be connected to the intranet 4 in the same manner. Each of the client terminals 3 includes, as its standard functions, a web browser 32 such as Internet Explorer and a mailer 31 such as Outlook Express, both of which are provided by Microsoft Corporation for example.

Although the network is the intranet 4 which is a closed network in one company or the like in the present embodiment, the Internet which is open to the outside may also be used. Of course, in the case where the Internet is used, further higher security properties than those for an intranet network are required. The computers which realize the PC 12 and the web server 2 in the analysis unit 1 do not have to be different but may be a single computer. The PC 12 and the web server 2 may be connected with a dedicated communication wire other than the intranet 4 (or the Internet). As just described, a variety of configuration modifications can be conceivable in the present embodiment.

Figure 2:
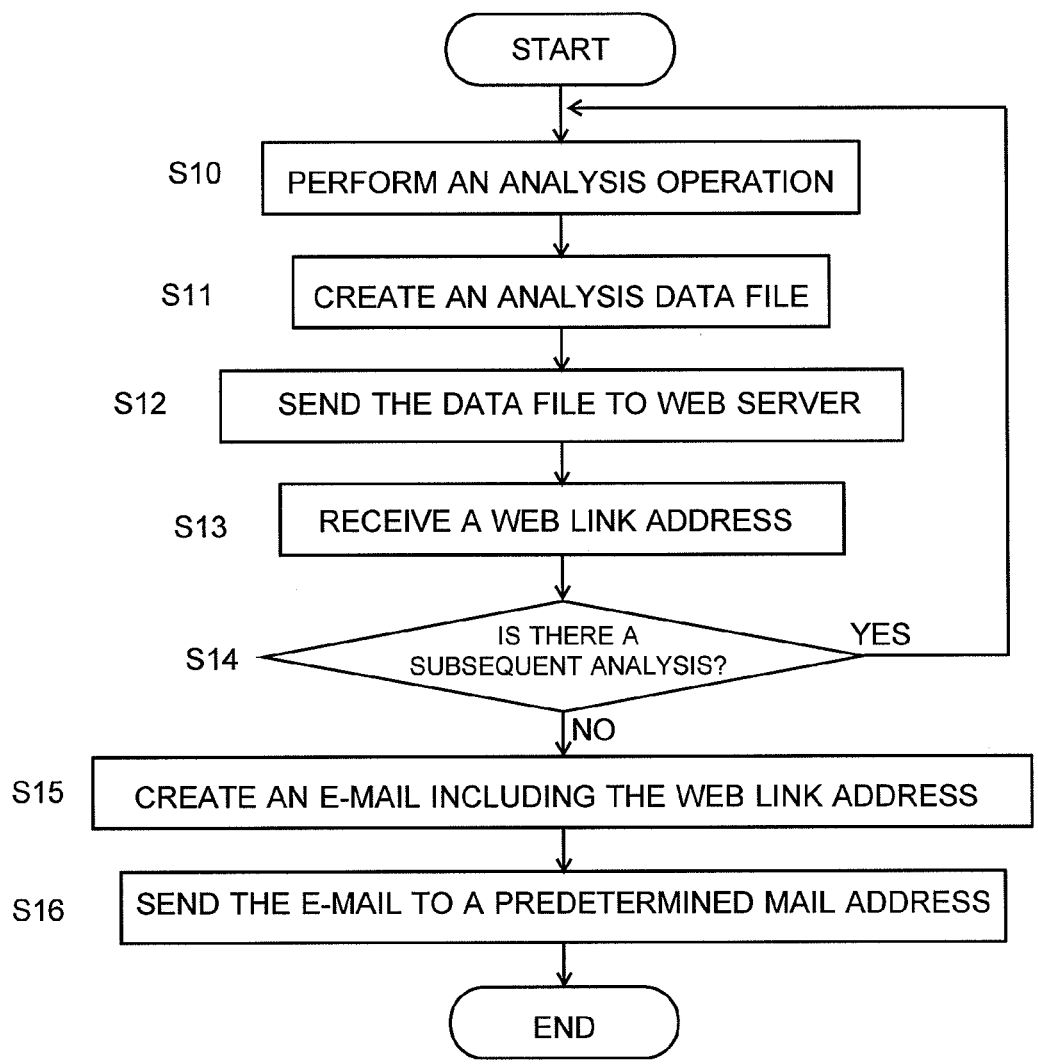
FIG. 2 is a flowchart illustrating the operation of the personal computer of the analysis unit in the system of FIG. 1.

Next, the operation of the present data management system will be explained with reference to the flowchart of FIG. 2. FIG. 2 is a flowchart illustrating the controlling/processing operation of the PC 12.

First, the GC/MS 11 in the analysis unit 1 performs an analysis in accordance with the analysis conditions set by the PC 12. In the present embodiment, it is presumed that a continuous analysis is performed, in which a number of samples to be analyzed are prepared and are individually selected in a predetermined order to be analyzed in the GC/MS 11.

When a series of the continuous analysis begins, the GC/MS 11 first performs an analysis for the first sample under the control of the PC 12 (Step S10). The data obtained by the analysis are sequentially sent to the PC 12 from the GC/MS 11, and the data are collected in the memory unit (not shown) in the PC 12. When the analysis for the first sample is completed, the analysis data file creator 13 in the PC 12 creates an analysis data file in a predetermined format (Step S11). The data file may include totally unprocessed data, i.e. what is called raw data, and processed data in which a predetermined data processing (for example, correction process, noise removal process, or other processes) is performed on the raw data. In addition, the data file may also include analytical data which are the result of an analytical processing such as a qualitative analysis and quantitative analysis. It is preferable that which data should be included in the data file may be set in advance.

When the data file is created, the file transfer processor 14 sends the data file to the web server 2 (Step S12). In this process, the original data are kept unchanged in the memory unit in the PC 12. The file transfer processor 22 in the web server 2 receives the data file transferred thereto and converts the data file into a predetermined format capable of being posted on a web page, e.g. into an HTML document format, and stores it in the web data memory 21. Simultaneously, the file transfer processor 22 sends the web page's storage location, i.e. link address information, to the analysis unit 1. In the analysis unit 1, the file transfer processor 14 receives the link address information and temporally stores it (Step S13).

Next, the PC 12 in the analysis unit 1 determines whether or not there is a subsequent analysis (Step S14), and in the case where one or more samples to be analyzed are left, the process returns to Step S10 and the processes of Steps S10 through S13 are repeated. Then, when the analyses for all the samples are completed, the process of S14 is determined to be YES and the process proceeds to Step S15, in which the e-mail creation processor 15 of the PC 12 receives, from the file transfer processor 14, the link address information corresponding to each of the data files which have been saved by then, and creates an e-mail in which the link address information is included in the body. After that, the e-mail creation processor 15 sends the e-mail to one or plural preset e-mail addresses (Step S16).

The e-mail sent is temporarily held in the mail server, which is not shown, by way of the intranet 4. When the user downloads and opens the e-mail sent to the e-mail address by using the mailer 31 on the client terminal 3 at hand, he or she finds the list of the link address information in the body of the e-mail. Then, the user performs a click operation with a pointing device such as a mouse on the link address corresponding to the data file whose contents are to be confirmed. With this operation, a command for viewing the web page of the link address is sent to the web server 2 by way of the intranet 4, and the access processor 23 in the web server 2 reads out the corresponding data from the web data memory 21 and sends them to the client terminal 3, which is the command source, by way of the intranet 4.

On the client terminal 3, the web browser 32 is automatically launched in response to the click operation for the link address, and on receiving the web page data, they are reconfigured and the web page is displayed on the window. The web page contains the analysis data that the user wants to see, and the user can view the analysis data by appropriately performing an operation such as a page scrolling. In the case where the user wants to see other analysis data, another link address listed in the body of the e-mail may be clicked.

With the aforementioned system, the user who has received an e-mail from the analysis unit 1 can view the desired analysis data using any client terminal 3 with only standard software. On the other hand, other persons who have not received an e-mail cannot view the analysis data since their storage location is unknown. Of course, a known security mechanism such as a user authentication function can be carried out according to necessity.

Figure 3:
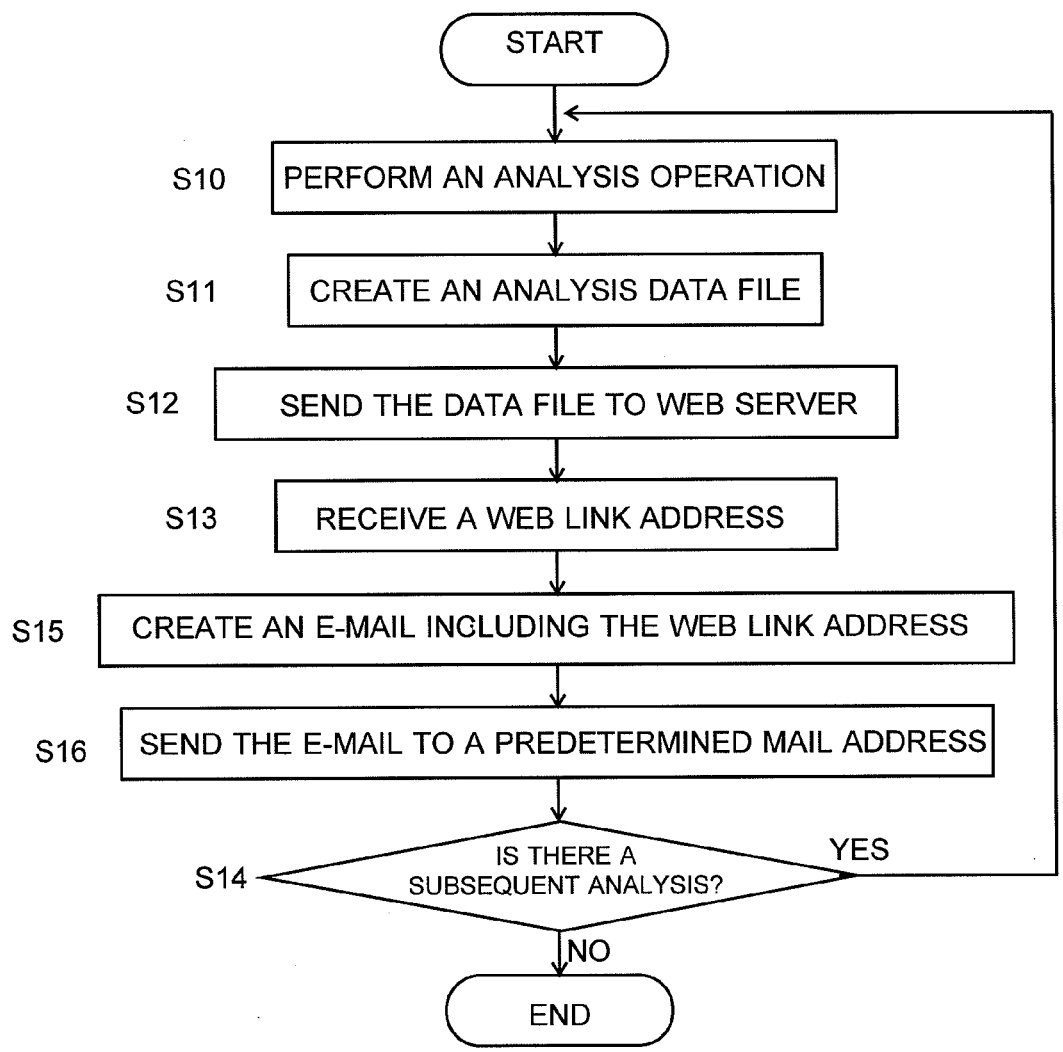
FIG. 3 is a flowchart illustrating the operation of another example of the personal computer of the analysis unit in the system of FIG. 1.

In the aforementioned embodiment, every time each analysis in a series of the continuous analysis is finished, a data file corresponding to the finished analysis is sequentially transferred from the analysis unit 1 to the web server 2 to be stored in the web data memory 21. However, an e-mail including the link address information is sent after the entire series of continuous analysis is finished. This is because, if an e-mail is sent each time in the case where the number of the analyses in the continuous analysis is large, the number of e-mails may become so large that receiving them is troublesome, which may possibly rather complicate the operation than simplify it. However, in the case where the number of the analyses is not large or in the case where the user wants to know the data of the finished analysis soon even in the middle of the continuous analysis, the operation in which an e-mail is sent every time an analysis is completed is more preferable. FIG. 3 illustrates a flowchart in which the operation is changed to such a manner.

That is, immediately after Step S13, the e-mail creation processor 15 of the PC 12 creates an e-mail including just-received link address information in its body and sends it to the previously-set one or plural e-mail addresses (Steps S15 and S16). After that, the PC 12 of the analysis unit 1 determines whether or not there is a subsequent analysis (Step S14), and in the case where a sample to be analyzed remains, the process returns to Step S10 and the operations of Steps S10, S11, S12, S13, S15, and S16 are repeated.

With such a change in the operation, an e-mail including the link address information which indicates the storage location of the analysis data is sent every time an analysis is completed, which allows the user to view the analysis data on the client terminal 3, while keeping up with the completion of the analysis. The user may be allowed to set on the PC 12 which method is adopted between those illustrated in FIG. 2 and FIG. 3.

It should be noted that the embodiment described thus far is an example and any modification, adjustment, and addition properly made in accordance with the spirit of the present invention will be included in the scope of the claims of the present application. For example, although the analyzing apparatus was GC/MS in the aforementioned embodiment, the present invention can be applied to a system using another analyzing apparatus as a matter of course.

The invention claimed is:

1. A data management system for an analyzing apparatus, including: a computer configured to control an analyzing apparatus and to receive data obtained by the apparatus; a web server realized by the computer itself or by another computer connected to the computer so that they can mutually communicate; and a network in which they are connected, the computer comprises:

a data transfer processor configured to transfer a data file created in accordance with a performance of an analysis by the analyzing apparatus to the web server; and an e-mail creator configured to create an e-mail including link information sent from the web server in correspondence to a data transfer by the data transfer processor and to send the e-mail over the network to a predetermined e-mail address; and, the web server comprises:

a web data transfer processor configured to convert the data file sent from the data transfer processor into a data format viewable on a web and for storing it in a web data memory;

a link information notifier configured to return link information for reading out data stored in the web data memory to the computer; and an access processor configured to, in the case where a readout command presenting link information regarding data stored in the web data storing means is received through the network, read out data corresponding thereto and for sending them to a command source;

the analyzing apparatus is measuring device; and the system is configured to perform, when a plurality of analyses are sequentially performed by the analyzing apparatus, the e-mail creator puts together, after all of a series of the analyses are completed without an intervening operation, pieces of link information received in correspondence to transfers of data files for all the analyses and sends them in one e-mail, in which each of the pieces of link information respectively corresponds to each of the data files.

2. The data management system according to claim 1, wherein the analyzing apparatus is a spectrometer.

* * * * *